United States Patent [19]

Ericson

[11] 4,396,374
[45] Aug. 2, 1983

[54] MATRIX BAND RETAINERS

[76] Inventor: Dan V. Ericson, Ehrensvärdsgatan 6, S-212 13 Malmö, Sweden

[21] Appl. No.: 415,175

[22] Filed: Sep. 7, 1982

[51] Int. Cl.³ .............................................. A61C 5/04
[52] U.S. Cl. .................................................... 433/39
[58] Field of Search ............................... 433/3, 23, 39

[56] References Cited

U.S. PATENT DOCUMENTS 3,411,214 11/1968 Lazarus ................................. 433/39
3,921,299 11/1975 Lazarus ................................. 433/39

Primary Examiner—Robert Peshock

[57] ABSTRACT

A retainer for securing in position a matrix band around a tooth comprises a body having an upper and a lower end surface, a through-bore which extends between the end surfaces and accommodates a spindle which is rotatable in the body and around which the matrix band can be wound and which has an axial slit starting from the proximal end of the spindle with respect to the lower end surface of the body and arranged for receiving the matrix band, a peripheral surface which is adapted to be applied against a tooth and has a first recess conformed to a first type of tooth, and a first channel which extends through the lower end surface, the first recess and the bore in order to permit the insertion of the matrix band in the channel and in the slit of the spindle from the lower end surface. The peripheral surface also has a second recess which is conformed to a second type of tooth. A second channel extends through the lower end surface, the second recess and the bore.

3 Claims, 9 Drawing Figures

MATRIX BAND RETAINERS

The present invention relates to a retainer for securing in position a matrix band around a tooth, comprising a body having an upper and a lower end surface; a through-bore extending between said end surfaces and accommodating a spindle which is rotatable in said body and around which the matrix band can be wound and which has an axial slit starting from the proximal end of the spindle with respect to said lower end surface of the body and provided for receiving the matrix band; a peripheral surface adapted to be applied against a tooth and having a first recess conformed to a first type of tooth; and a first channel extending through said lower end surface, said first recess and said bore so as to allow the insertion of the matrix band in the channel and the slit of the spindle from said lower end surface of the body.

Matrix bands are used by dentists in order to contour fillings, prevent excess of filling material and to allow amalgam condensation. The different matrix bands available on the market are used daily by all dentists. There are several different types of matrix band retainers which are employed in order to hold the matrix band in place and tighten it around the tooth. The retainer hitherto most frequently used, viz. the so-called Nyström retainer, is difficult, not to say impossible to apply to the inner side of the teeth located to the front of the mouth cavity. This retainer is used exclusively to retain matrix bands for amalgam fillings. For tooth-colored filling materials in the front teeth, there are no matrix band retainers which can offer a stable matrix system that can be readily applied to the tooth before the filling has set.

The main object of the present invention is to provide a matrix band retainer which can be used at the inner and outer sides of the tooth row in both the buccal and the front teeth area, is easy to apply and is secured firmly also at fillings in the front teeth.

A further object of the invention is to provide a matrix band retainer which is conformable to different tooth shapes.

Yet another object is to provide a device which permits safely retaining a matrix band around a tooth in the posterior part of the oral cavity and which can be operated by the dentist from a location outside the mouth.

According to the invention, these objects are achieved by the provision of a matrix band retainer in which a second recess is provided in the peripheral surface and conformed to a second type of tooth, and a second channel extends through the lower end surface, the second recess and the bore.

According to another aspect of the invention, the channels taper towards the lower end surface, whereby the matrix band when being tightened by means of the spindle will be drawn tightest against the lower portion of the tooth.

According to yet another aspect of the invention the head of the spindle has a groove for receiving operating means for actuating the spindle from a location outside the oral cavity.

Owing to its simple construction, the matrix band retainer according to the invention is readily manufactured at a low cost from both plastic and metal.

The invention will be described in greater detail hereinbelow with reference to the accompanying drawings showing an embodiment of the invention and in which.

Figure 1:
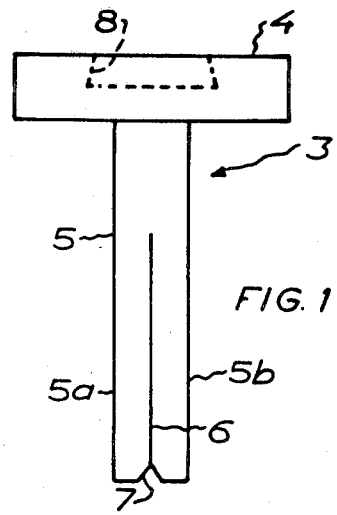
FIG. 1 is a side view of a spindle for tightening a matrix band around a tooth.
Figure 2:
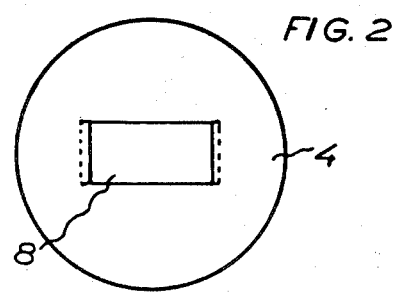
FIG. 2 is a top plan view of the spindle in FIG. 1.
Figure 9:
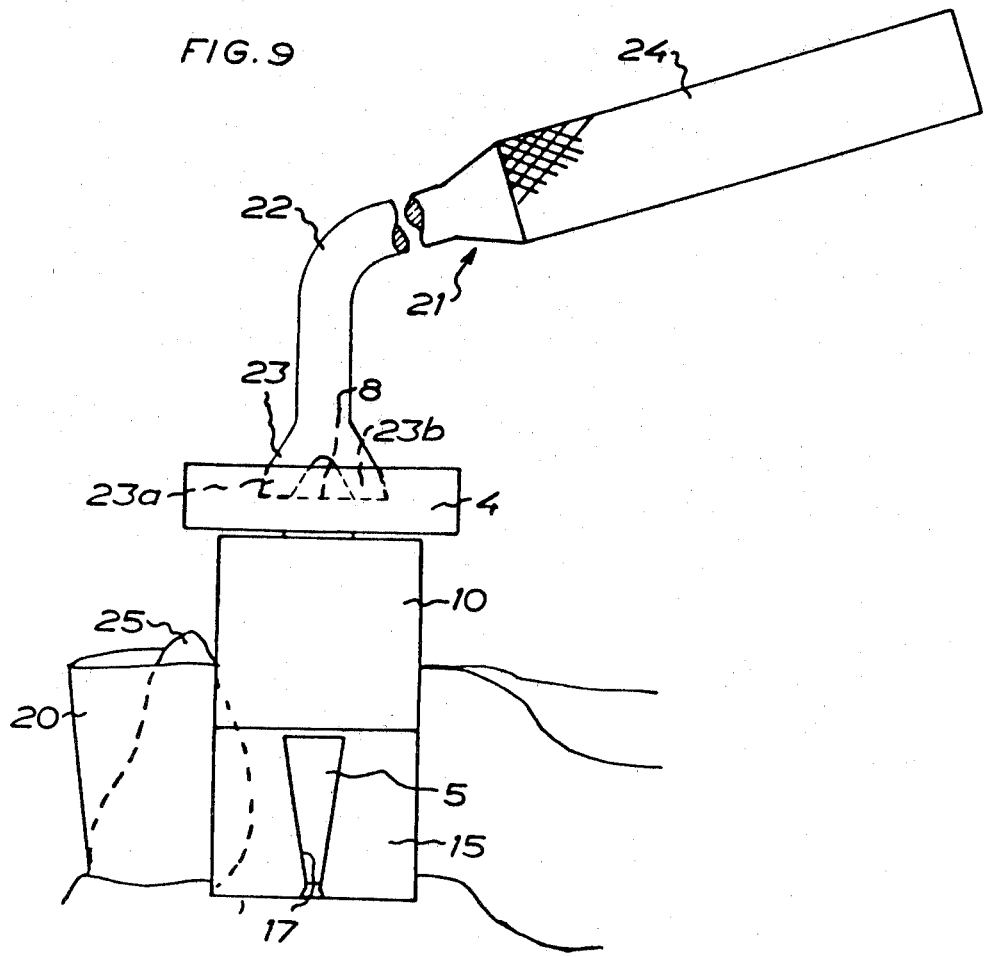
FIG. 9 shows the matrix system in FIG. 7 and operating means connectible to the matrix band retainer.

In FIGS. 1 and 2, there is shown a spindle 3 on which a matrix band is wound and drawn tight around a tooth (FIG. 7) and which forms a first part of the matrix band retainer according to the invention. The spindle consists of a discoid head 4 and a shaft 5. The head has a groove 8 in which one end of an operating means 21 (FIG. 9) can be inserted so as to permit turning the spindle by this operating means when the matrix band retainer is applied against a tooth far back in the oral cavity. The shaft 5 is slit so as to form two shanks 5a, 5b separated by a vertical slit 6 for receiving the matrix band. A V-shaped notch 7 in the lower portion of the shaft facilitates the introduction of the matrix band.

Figure 3:
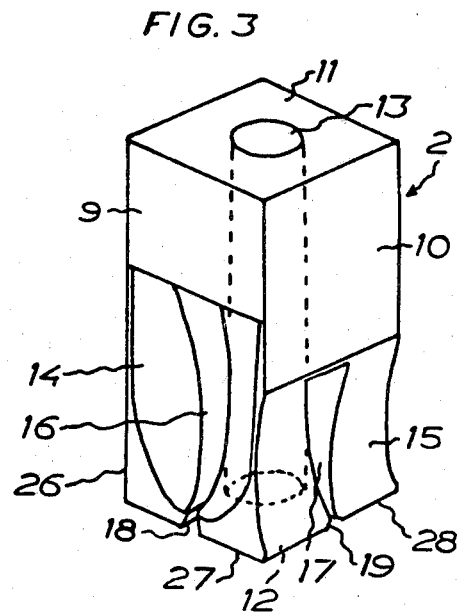
FIG. 3 shows a matrix band retainer body which, together with the spindle, constitutes the matrix band retainer proper.
Figure 4:
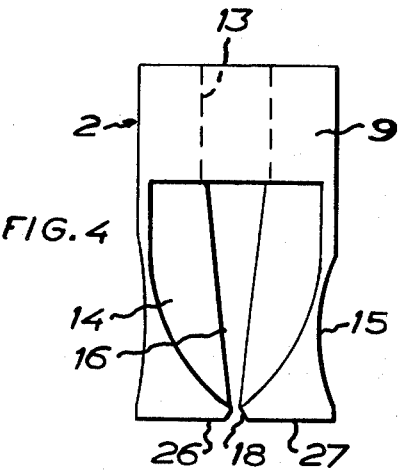
FIGS. 4 and 5 are two side views of the body in FIG. 3.
Figure 5:
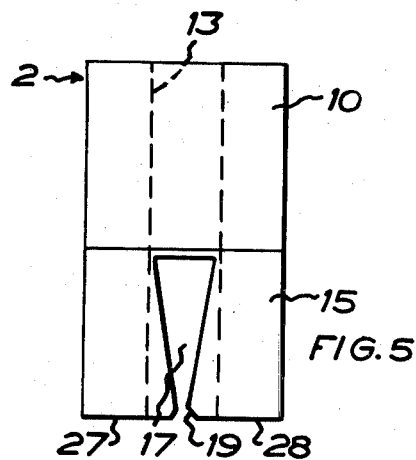

FIGS. 3, 4 and 5 show a parallelepipedal body 2 which is the second part of the matrix band retainer. In these figures, there are only shown two lateral surfaces 9, 10 and an upper and a lower end surface 11 and 12, respectively. The body 2 has a cylindrical axial through-bore 13 extending between the end surfaces 11 and 12 and adapted to accommodate the shaft 5 of the spindle 3. The lateral surface 9 has a concave recess 14 the shape of which is conformed to the buccal surface of the front teeth. The surface (not shown) of the body which is located opposite the surface 9 has a recess which is conformed to the buccal surface of the canines. The lateral surface 10 has a recess 15 which is conformed to the buccal and lingual surfaces of the molars. The surface (not shown) of the body which is opposite the surface 10 has a recess which is conformed to the buccal and lingual surfaces of the premolars. With these four recesses it is possible to otbtain a suitable fit of the body 2 against the tooth around which the matrix band is to be placed. The recesses are located at the lower portion of the body in conjunction with the lower end surface 12, and the lower portion of the body is split by two vertical channels 16, 17 which are cut through the lower end surface 12, the respective recess 14 and 15 and the bore 13 where they intersect at right angles. The channels taper downwards towards the lower end surface for reasons which will be discussed in greater detail hereinbelow.

Like the inlet to the slit 6 in the shaft 5 of the spindle 3, the inlets to the channels 16 and 17 are designed as V-shaped notches 18, 19 which facilitate the insertion of the matrix band in the channels.

The channel 16 extends higher than the channel 17, the channel 16 being used for the plastic matrix bands available on the market, while the channel 17 is used for the steel matrix bands available on the market.

By the provision of channels 16 and 17 in the lower portion of the body 2, there are obtained four elastic legs 26–29 which will rest two by two against a tooth once the matrix band has been secured around it.

Figure 6:
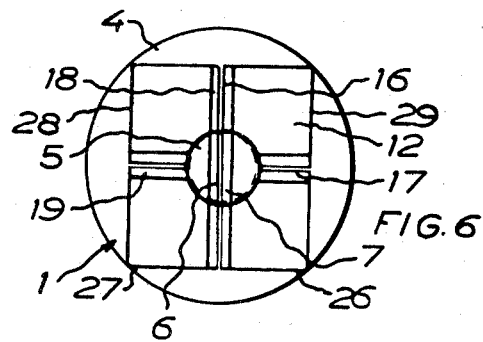
FIG. 6 shows the matrix band retainer according to the invention from underneath and illustrates the relative position between the spindle and the body that permits the insertion of the matrix band in the retainer.

In FIG. 6, the matrix band retainer 1 according to the invention is shown from below with the spindle 3 inserted in the bore 13. The spindle has been turned so as to align its slit 6 with the first channel 16. Now, the matrix band can be readily passed up into the channel 16 and the slit 6.

Figure 7:
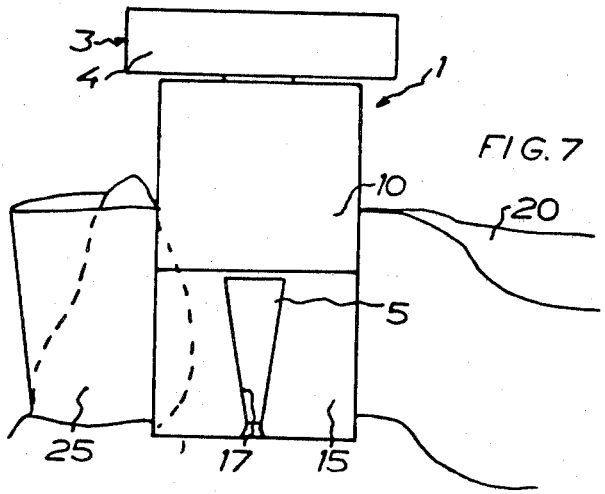
FIG. 7 is a side view of a matrix system with a matrix band and a matrix band retainer which secures the matrix band in position around a tooth.

In FIG. 7, there is shown a matrix system with a matrix band retainer 1 tightening a matrix band 20 around a tooth 25. For this tooth use is made of the recess 14 whose shape is conformed to the surface of the tooth. When the matrix band retainer 1 has been passed vertically down over the band, such that it is inserted in the channel 16 and the slit 6 of the spindle 3, the band is tightened by turning the head 4 of the spindle. By the wedge shape of the channel 16, the matrix band 20 will be drawn tighter cervically than coronally, thus securing the band firmly in position on the tooth.

Figure 8:
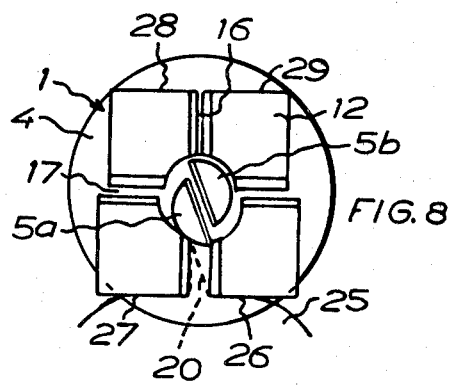
FIG. 8 shows the matrix band retainer in FIG. 7 from underneath, the matrix band being only intimated to avoid crowding of the drawing.

In FIG. 8, the matrix band retainer 1 applied to the tooth 25 is shown from underneath, the matrix band 20 being merely intimated by dashed lines in the channel 16. When the spindle is turned and the matrix band is wound up on the spindle shaft 5, the elastic legs 26 and 27 are urged slightly apart, so that the recess will become further conformed to the shape of the tooth, which contributes to firmly maintaining the matrix band retainer in place.

The spindle 3 is locked in the body 2 in different ways. First, there is frictional engagement between the matrix band wound on the shaft and the wall of the bore 13. Secondly, the spindle will slightly tilt in the bore 13 since the matrix band is wound on the lower part of the shaft 5. Thirdly, the shanks 5a and 5b of the shaft will be shorn apart by the traction of the matrix band and, as a result of this tractive force, one shank 5 will be slightly squeezed into the widened inlet of the channel 16. Fourthly, the risk of unintentional loosening of the matrix band will be reduced in that the cylindrical shape of the shaft 5 is abolished when the matrix band is tightened.

When the matrix band is to be drawn tight around a tooth in the posterior region of the oral cavity, use is made of an operating means 21. It consists of an elongate flexible operating arm 22, one end of which is designed as a handle 24 and the opposite end 23 of which is designed as a cloven hoof with two projections 23a, 23b. This hoof-shaped end fits in the groove 8 in the spindle head 4. With the aid of the operating means, the dentist can turn the spindle from a location outside the mouth, which facilitates the application of the matrix system around a tooth far back in the mouth.

The matrix band for incisives and canines is placed around the tooth and its ends are held together, so that the matrix band retainer can be passed over the matrix band from above. This is a rapid method of application, making it possible to use the matrix system also for tooth-colored filling materials.

When the matrix band retainer is used for holding steel matrix bands for amalgam fillings, the matrix band is first wound half a revolution on the retainer and is only then passed around the tooth.

By its compactness and stability, the matrix band retainer according to the invention can be placed at the inner side of the row of teeth also far to the front of the oral cavity. This possibility is highly restricted in other prior-art retainers for amalgam matrix bands.

What I claim and desire to secure by Letters Patent is:

1. Retainer for securing in position a matrix band (20) around a tooth, comprising a body (2) having an upper and a lower end surface (11, 12); a through-bore (13) extending between said end surfaces and accommodating a spindle (3) which is rotatable in said body and around which the matrix band can be wound and which has an axial slit (6) starting from the proximal end (5a, 5b) of the spindle with respect to said lower end surface (12) of the body and provided for receiving the matrix band; a peripheral surface (9, 10) adapted to be applied against a tooth and having a first recess (14) conformed to a first type of tooth; and a first channel (16) extending through said lower end surface, said first recess and said bore so as to allow the insertion of the matrix band (20) in the channel and the slit of the spindle from said lower end surface of the body, characterized by a second recess (15) provided in the peripheral surface (10) and conformed to a second type of tooth, and a second channel (17) extending through the lower end surface (12), the second recess and the bore (13).

2. Retainer as claimed in claim 1, characterized in that the channels (16, 17) taper towards the lower end surface (12), whereby the matrix band (20) when being tightened by means of the spindle (3) will be drawn tightest against the lower portion of the tooth (25).

3. Retainer as claimed in claim 1 or 2, characterized in that the head (4) of the spindle (3) has a groove (8) for receiving operating means (21) for actuating the spindle from a location outside the oral cavity.

* * * * *